United States Patent [19]
Floss et al.

[11] Patent Number: 6,150,568
[45] Date of Patent: Nov. 21, 2000

[54] VALIOLONE, A METHOD OF PREPARING IT, AND ITS USE TO PREPARE ACARBOSE AND VOGLIBOSE

[75] Inventors: Heinz G. Floss, Bellevue; Sungsook Lee, Seattle, both of Wash.; Ingo Tornus, Hennigsdorf, Germany

[73] Assignee: University of Washington, Seattle, Wash.

[21] Appl. No.: 09/280,454

[22] Filed: Mar. 30, 1999

Related U.S. Application Data

[60] Provisional application No. 60/080,134, Mar. 31, 1998, abandoned.

[51] Int. Cl.$^7$ .............................. C07C 35/14; C07C 35/16
[52] U.S. Cl. ......................... 568/833; 568/347; 568/376; 514/61; 536/17.2; 536/18.6; 536/18.7
[58] Field of Search .................................. 536/17.2, 18.6, 536/18.7; 568/347, 376, 833; 514/61

[56] References Cited

U.S. PATENT DOCUMENTS

| | | | |
|---|---|---|---|
| 4,595,678 | 6/1986 | Horii et al. | 514/53 |
| 4,824,943 | 4/1989 | Horii et al. | 536/1.1 |
| 4,898,986 | 2/1990 | Horii et al. | 568/376 |
| 5,004,838 | 4/1991 | Horii et al. | 568/347 |
| 5,456,920 | 10/1995 | Matoba et al. | 424/465 |

OTHER PUBLICATIONS

Fukase et al.(I), "Synthesis of a Branched–Chain Inosose Derivative, a Versatile Synthon of N–Substituted Valiolamine Deivative from D–Glucose," *Journal of Organic Chemistry*, 57(13), 3642–3650 (Jun. 19, 1992).

Kameda et al., "Valiolamine, A New a–Glucosidase Inhibiting Aminocyclitol Produced by *Streptomyces Hygroscopus*," *The Journal of Antibiotics*, 37(11), 1301–1307 (Nov. 1984).

Iwasa et al., "Studies on Validamycin, New Antibiotics. II—Production and Biological Properties of Validamycins A dn B," *The Journal of Antibiotics*, 24(2), 107–113 (Feb., 1971).

Asano et al., "Microbial Degradation of Validamycin A by *Flavobacterium Saccharophilum*—Enzymatic Cleavage of C–N Linkage in Validoxylamine A," *The Journal of Antibiotics*, 37(8), 859–867 (Aug., 1984).

Horii et al. (V), "Stereoselective Conversion of Valienamine and Validamine Into Valiolamine," *Carbohydrate Research*, 140, 185–200 (1985).

Cheng, "Section VII—Trends and Perspectives," Ch. 31 in *Annual Reports of Medicinal Chemistry*, Bristol (ed.), 1994, only pages 312–313 supplied.

Balfour et al., "Acarbose—An Update of its Pharmacology and Therapeutic Use in Diabetes Mellitus," *Drugs*, 46(6), 1025–1054 (1993).

Fukase et al, (II), Synthesis of Valiolamine and Its N–Substituted Derivative AO–128, Validoxylamine G, and Validamycin G via Branched–Chain Inosose Derivatives, *Journal of Organic Chemistry*, 57(13), 3651–3658 (Jun. 19, 1992).

Köhn et al., "4–Alkylamino–4,6–didesoxyzucker Durch Reduktiv Aminierung," *Justus Liebig's Annalen de Chemie*, 1985, (Issue No. 4), 775–784 (Apr. 15, 1985).

Budavari et al. (eds.), *The Merck Index, 11th Edition*, Merck & Co., Inc., Rahway, NJ, 1989, only title and text pages 4 and 1558–1559 supplied.

*Primary Examiner*—Gary Geist
*Assistant Examiner*—L. Eric Crane
*Attorney, Agent, or Firm*—Norris, McLaughlin & Marcus, P.A.

[57] ABSTRACT

Disclosed is the compound valiolone, which has the formula (I):

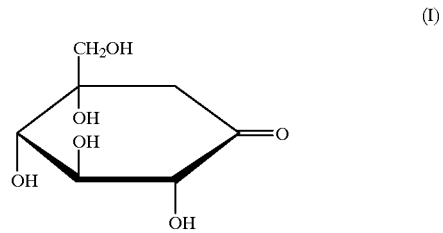

a method of preparing valiolone, and a method of using valiolone to prepare acarbose and voglibose.

12 Claims, No Drawings

VALIOLONE, A METHOD OF PREPARING IT, AND ITS USE TO PREPARE ACARBOSE AND VOGLIBOSE

This application claims the benefit of Provisional Application No. 60/080,134, filed on Mar. 31, 1998, now abandoned.

The present invention relates to valiolone, which has the formula:

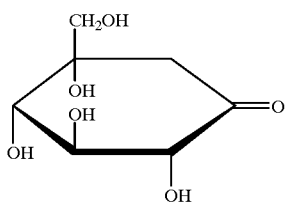

(I)

to a method of preparing valiolone, and to a method of using valiolone to prepare acarbose and voglibose.

It is known that the antibiotic validamycin can be produced by fermentation of *Streptomyces hygroscopicus* subsp. *limoneus* (Studies on Validamhycins, New Antibiotics II, T. Iwasa et al., Journal of Antibiotics, Vol 24, No. 2 pps. 107–113) 1971. In the search for aminocylitols in the above mentioned fermentation broth, the α-glucosidase inhibiting aminocyclitol valiolamine was isolated (Valiolamine, A New α-Glucosidase Inhibiting Aminocyclitol, Yo Kameda et al., Journal of Antibiotics, Vol. 37, No. 11, pps. 1301–1307) 1984. Valiolamine (II) has the structure

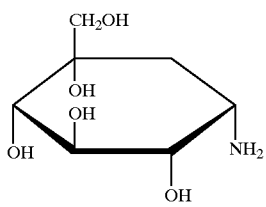

(II)

Valiolamine is a natural product which can be isolated from fermentations of *Streptomyces hygroscopicus*.

Valiolamine can be prepared by the biodegradation of validamycin to a mixture of validamine and valienamine (N. Asano et al., V. Antibiot, 37, 859–867 (1984)) which is then converted chemically into valiolamine (S. Harii et al., Carbohyds Res. 140, 185–200 (1985)).

It is known that (1S)-(1(OH),2,4/1,3)-2,3,4-tri-O-benzyl-1-C[(benzyloxy)methyl]-5-oxo-1,2,3,4-cyclohexanetetrol is an important compound in the synthesis of valiolamine and its N-substituted derivatives (Synthesis of a Branched-Chain Inosose Derivative, A Versatile Synthon of N-Substituted Valiolamine Derivatives from D-Glucose, H. Fukase et al., J. Org. Chem. 1992, 57, 3642–3650). This compound can be depicted by the formula

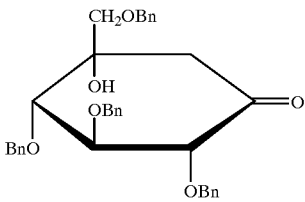

(III)

The antidiabetic drug voglibose can be synthesized from compound III above though no such process is known for the drug acarbose.

In accordance with the invention, a new compound which can be used to prepare voglibose as well as the drug acarbose has been discovered which has been given the name valiolone and which can be represented by the formula I:

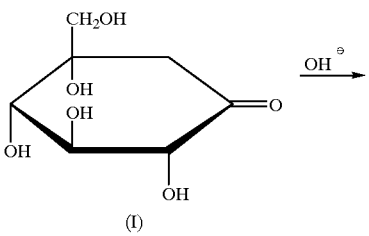

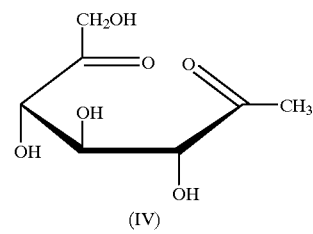

Valiolone can be prepared by an oxidative deamination of valiolamine. The procedure involves oxidation of valiolamine (II), in theory, to an intermediate imine, which is hydrolyzed to the ketone (I) under mild acidic conditions.

Oxidizing agents which are known to be effective in converting amines to imines can be used. These are illustrated by 3,5-di-t-butyl-1,2-benzoquinone (DBQ), nicotinic aldehyde in the presence of a base (such as 1,8-diazabicyclo[4.3.0]undec-7-ene[DBU] or triethyl amine), benzothiazole-2-aldehyde and the like. The oxidation reaction proceeds easily generally without heat but heat can be used if desired, such as from room temperature up to about 50° C. The reactions can be conducted with (preferably) or without an appropriate solvent. The solvents can be illustrated by alcohols such as methanol, ethanol, isopropanol and the like. The intermediate can be isolated but preferably it is not isolated and is hydrolyzed in situ in the reaction mixture to produce the desired valiolone. Hydrolysis proceeds using known reagents and conditions for hydrolyzing an imine to a ketone. Mild acidic conditions (about pH 4–6 and more preferably of about 5 pH) can be used for hydrolysis. Oxalic acid and acids of similar $pK_a$ that allow good buffering within the pH range of about 4 to 6 and preferably 4.5 to 5.5 can be used. Acids, preferably an organic acid, which can be used include oxalic acid, acetic acid, malonic acid, formic acid, as well as inorganic acids and acidic compounds, such as HCl, $H_2SO_4$, wet silica gel, and the like. The type of acid used can be readily selected by one of ordinary skill. The pH range selected can be guided by the qualification that a significantly more acidic pH can allow for the competing dehydration of valiolone or the intermediate imine. If the pH is allowed to become too basic, yields can decrease, in theory because hydrolysis becomes more sluggish and the possibility of a retroaldol cleavage as a side reaction increases. It has been found that between these two extremes there is a narrow pH range in which both decomposition reactions are sufficiently slow to allow for effective product recovery.

The valiolamine (II) is preferably unprotected when oxidized. While a variety of oxidizing agents can be used, preference is given to 3,5-di-t-butyl-1,2-benzoquinone (DBQ). Likewise, a variety of hydrolysis agents can be used to convert the imine to the ketone, but preference is given to oxalic acid. Further, the preferred reaction scheme requires careful control of the pH in the hydrolysis step to about 5.0.

In view of the foregoing, a preferred scheme for preparing valiolone is as follows:

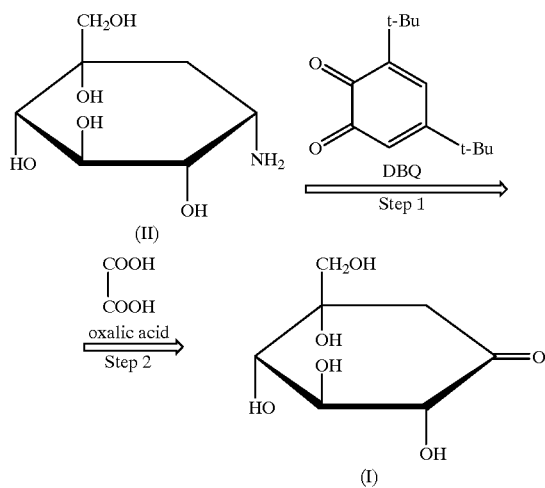

The successful preparation of valiolone is surprising because several structural features of this compound suggest that this compound might be unstable, or be susceptible to dehydration or retroaldol reaction unless prepared in protected form. Surprisingly, however, it has been found that valiolone, in unprotected form, is achieved in good yields according to the scheme set forth above.

In theory, the structural feature which is responsible for the easy dehydration of valiolone is the presence of a tertiary alcohol function on a carbon β to the carbonyl group. The dehydration follows a general acid catalysis mechanism and occurs upon exposure of the imine intermediate in the preparation of valiolone to a pH significantly more acidic than the desired pH. The retroaldol reaction that valiolone would likely undergo is shown below. It results in a ring opening of the original cyclic structure.

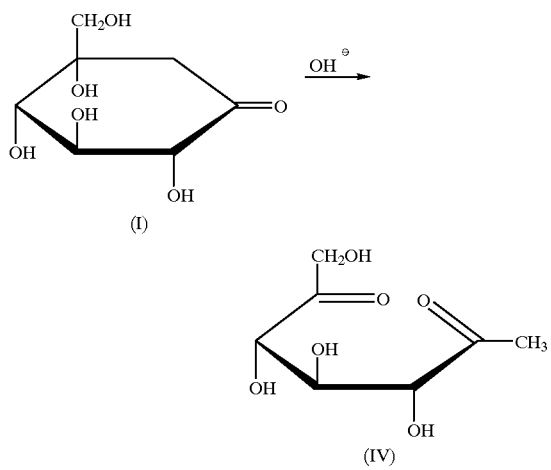

Valiolone is useful as an intermediate in the preparation of the drugs acarbose and voglibose. Voglibose can be prepared by reacting valiolone with 2-amino-1,3-propanediol (serinol) in the presence of a reducing agent, preferably $Na(CN)BH_3$, with or without an acid catalyst (e.g., acetic acid, HCl), according to the following schematic reaction:

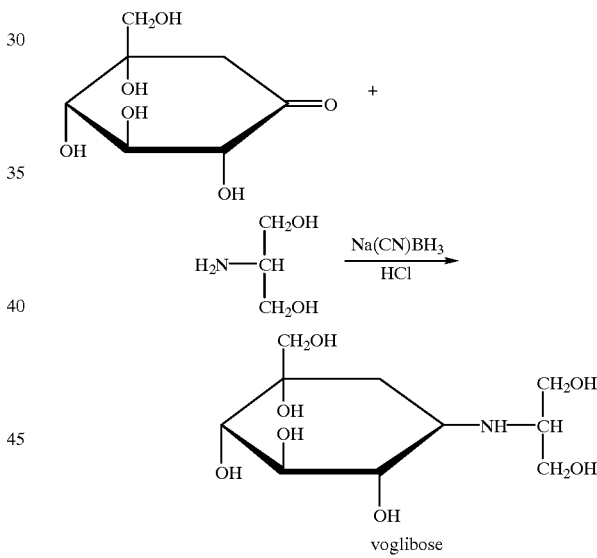

Acarbose can be prepared by reacting valiolone with the glycoside 4"-amino-4",6"-dideoxymaltotriose (V) in the presence of an acid at a pH within the range of 1–4 followed by reacting the intermediate (VI) with a reducing agent such as $Na(CN)BH_3$ in the presence of a modifying agent, e.g., $CeCl_3$ as per the following schematic reaction:

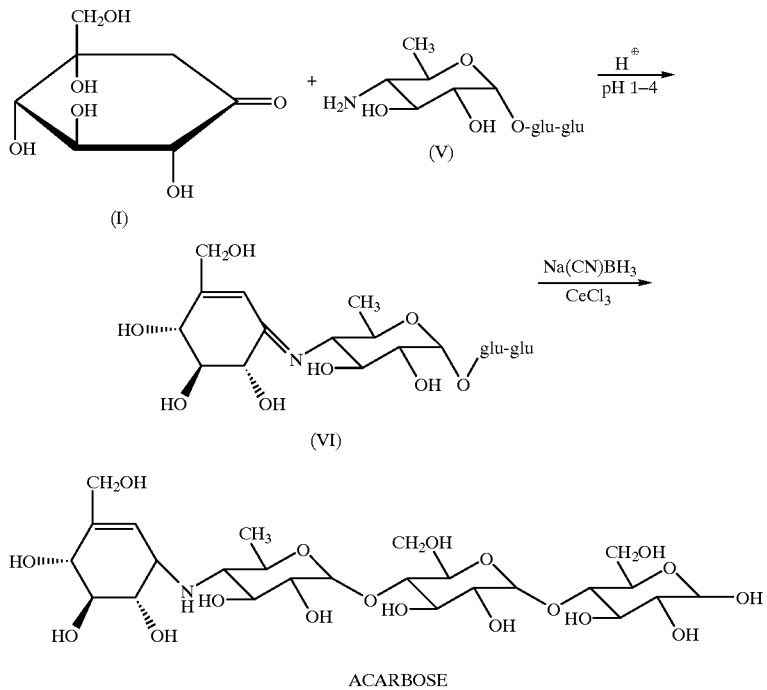

ACARBOSE

Voglibose is useful for the treatment of postprandial hyperglycemia in diabetic patients (Annual Reports of Medicinal Chemistry 1995, page 313). Acarbose is useful in the treatment of non-insulin-dependent diabetes mellitus (Drugs 46, 1025–1054, 1993).

The invention will now be further described with reference to the following:

EXAMPLE 1—SYNTHESIS OF VALIOLONE

Example 1

To a stirred solution of valiolamine (80 mg, 0.414 mmol), in 96% aq. methanol (5.2 mL) was added 3,5-di-t-butyl-1,2-benzoquinone (92 mg, 0.418 mmol) dissolved in methanol (2 mL) at room temperature. After stirring for 90 min, water (1 mL) was added, the pH lowered to 5.0 (pH paper control) with an aqueous solution of oxalic acid, and the mixture shaken vigorously for 45 min. Subsequently, the pH was adjusted to 8 with ammonium hydroxide. The mixture was diluted with water (80 mL) and extracted with chloroform (4×40 mL). The water phase was concentrated to approximately 5 mL in a vacuum and loaded onto an IRA-68 anion exchange column (40 mL, OH⁻-form). Elution with water gave a fraction containing the product. This solution was concentrated to 1 mL and further purified by chromatography on a weak cation exchanger (Wk-100, 40 mL, $NH_4^+$-form, mobile phase: water) to give pure valiolone (42 mg, 0.219 mmol, 53% yield). $^1$H NMR (300 MHz, $D_2O$), δ(ppm): 2.39 (d, 1H, J=14.6 Hz, HCH—C=O); 2.79 (d, 1H, J=14.6 Hz, HCH—C=O); 3.3 (d, 1H, J=11.5 Hz, HCH—C—OH); 3.62 (d, 1H, J=11.3 Hz, HCH—C—OH); 3.63 (t, 1H, J=9.5 Hz, HC-3); 3.84 (d, 1H, J=9.4 Hz, HC-4) and 4.19 (d, 1H, J=9.7 Hz, Hc-2). $^{13}$C NMR (75 MHz, $D_2O$), δ (ppm): 45.45, 64.37, 72.91, 75.79, 76.01, 78.62 and 209.43.

EXAMPLE 2—SYNTHESIS OF VOGLIBOSE

Example 2

The valiolone of the invention can be used to prepare voglibose by the following procedure.

To a solution of 5 mmol of valiolone and 5 mmol of 2-amino-1,3-propanediol in 25 mL DMF or methanol is added a catalytic amount of HCl. After 1 hour at room temperature, 2.5 mmol of solid $Na(CN)BH_3$ is added and the reaction mixture is stirred over night at room temperature. The reaction mixture is then concentrated under reduced pressure and the residue is dissolved in water and applied to a Dowex 50 (H⁺) column. The column is washed with water and the product is eluted with 0.5 N $NH_4OH$. After concentrating the eluate, the residue is dissolved in water and applied successively first to a Amberlite CG-50 ($NH_4^+$) or Diaion WK-100 ($NH_4^+$) and then a Dowex 1 (OH⁻) column and each time the product is eluted with water to give voglibose.

It will be appreciated that the instant specification and claims are set forth by way of illustration and not limitation, and that various modifications and changes may be made without departing from the spirit and scope of the present invention.

What is claimed is:

1. The compound valiolone, which has the formula (I):

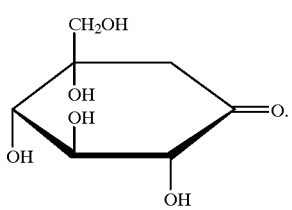

2. A process for preparing the compound according to claim 1, said process comprising reacting valiolamine of the formula (II):

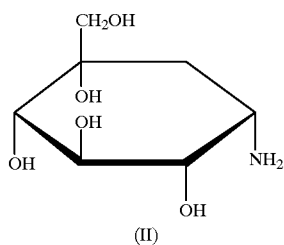

(II)

with an oxidizing agent followed by hydrolyzing the above reaction product under mild acidic conditions, to yield valiolone (I).

3. The process according to claim 2, wherein the oxidizing agent is 3,5-di-t-butyl-1,2-benzoquinone.

4. The process according to claim 2, wherein the hydrolysis is effected by oxalic acid with control of the pH to about 5.0.

5. The process according to claim 2, wherein the hydrolysis reaction is conducted within a pH ranging from about 4.5 to about 5.5.

6. A process for preparing voglibose from the valiolone compound according to claim 1, said process comprising reacting said valiolone with 2-amino-1,3-propanediol in the presence of a reducing agent.

7. A process for preparing acarbose from the valiolone compound of claim 1, said process comprising reacting said valiolone with 4"-amino-4",6"-dideoxymaltotroise under acidic conditions within a pH range of from about 1 to about 4 to form a reaction intermediate followed by reacting the reaction intermediate in the presence of a reducing agent to form acarbose.

8. The process according to claim 6, wherein the reducing agent is $Na(CN)BH_3$.

9. The process according to claim 7, wherein the reducing agent is $Na(CN)BH_3$.

10. The process according to claim 7, further comprising reacting the reacting intermediate with the reducing agent in the presence of $CeCl_3$.

11. The process according to claim 8, further comprising reacting valiolone with 2-amino-1,3-propanediol in the presence of a reducing agent and in the presence of $CeCl_3$.

12. The process according to claim 9, further comprising reacting the reaction intermediate with the reducing agent in the presence of $CeCl_3$.

* * * * *